United States Patent [19]

ElFeraly et al.

[11] Patent Number: 4,952,603

[45] Date of Patent: Aug. 28, 1990

[54] **METHOD FOR THE ISOLATION OF ARTEMISININ FROM *ARTEMISIA ANNUA***

[76] Inventors: Farouk S. ElFeraly, 105 Virginia St.; Hala N. ElSohly, 41 Shelia Dr., both of Oxford, Miss. 38655

[21] Appl. No.: 208,763

[22] Filed: Jun. 20, 1988

[51] Int. Cl.$^5$ .............................................. A61K 31/335
[52] U.S. Cl. ..................................................... 514/450
[58] Field of Search ......................................... 514/450

[56] References Cited

PUBLICATIONS

Acton et al., J. Chrom., 355 (1986), 448–450.
Merck Index, 9th ed., p. 931, No. 6972, 1976.

*Primary Examiner*—John W. Rollins
*Attorney, Agent, or Firm*—William D. Stokes

[57] ABSTRACT

An improved method of producing artemisinin, an antimalarial agent, from the leaves of the plant *Artemisia annua* 1. comprising extracting the leaves of the plant with hexane, partitioning the hexane between hexane and acetonitrile following chromatographing the acetonitrile phase to produce substantially pure artemisinin.

12 Claims, No Drawings

METHOD FOR THE ISOLATION OF ARTEMISININ FROM *ARTEMISIA ANNUA*

BACKGROUND OF THE INVENTION

Artemisinin (Qinghaosu) is a novel sesquiterpene lactone endoperoxide having potent antimalarial activity. Artemisinin is obtained from the leaves of *Artemisia annua* l.,the well known traditional Chinese herbal remedy, Qinghao. The only reported method of extraction of artemisinin has been by ethyl ether. Moreover, literature has provided no details of any method of isolation of artemisinin. Investigators working at the Walter Reed Army Institute of Research located *Artemisia annua* growing in the Washington, D.C. area and reported two procedures for the isolation of artemisinin. One of those procedures depends upon the use of the Ito multi-layer separator extractor. This procedure is only suitable for small scale production. The second procedure, while being capable of producing relatively larger quantities of artemisinin, suffers from major disadvantages, among which is that the procedure depends upon chromatographing a relatively crude fraction on silica gel. This known technique necessitates the use of a large ratio of solute to adsorbent, for example, the order of 1:44. Another disadvantage is that the solvent system used in eluting the chromatographic column is 7.5% ethyl acetate in chloroform, accordingly, the bulk of the eluting system is chloroform which is dense, expensive and unstable. Moreover, the order of elution when using such solvent system is artemisinin ($R_f$ 0.83), arteannuin B (R 0.72) and the artemisinic (qinghao) acid (R 0.6). The acid being predominant, tends to elute with artemisinin, accordingly the fractions contain large amount of the acid that affects the purity of the desired artemisinin.

It is the principal objective of this invention to provide a simple, practical method for the isolation and recovery of artemisinin from plant material which yields artemisinin in quantities and purity heretofore unobtainable in the methods known in the art.

Still another objective of the invention is the provision of a method for the isolation and recovery of artemisinin which method allows the eluting columns to be reused resulting in enormous savings heretofore impossible using the know methods.

SUMMARY OF THE INVENTION

The invention is a method for the production of artemisinin from the plant, *Artemisia annua* comprising the steps of extracting leaves of the plant with hexane, partitioning the hexane extract between hexane and acetonitrile, evaporation of the acetonitrile fraction followed by chromatographing the evaporated fraction on a silica gel using as an eluting solvent a mixture of ethyl acetate in hexane followed by evaporation and crystallization to yield pure artemisinin.

DETAILED DESCRIPTION OF THE INVENTION

In accordance with the method of the invention, dried leaves of *Artemisia annua* are extracted with hexane. The twigs or stems of the plant, comprising about 80% of the plant are not extracted for the reason that it was found that the twigs or stems contained little or no artemisinin. In the preferred embodiment of the invention, the extract is then partitioned in order to concentrate the extract and remove as many impurities as possible from the concentrate. This intermediate step of partitioning greatly facilitates and improves the efficiency of the chromatographic separation step.

Partitioning of the hexane extract is carried out using presaturated hexane and aqueous acetonitrile. For each 1g of material to be partitioned, a ratio of 12ml hexane to 4ml of 20% aqueous acetonitrile gives excellent results. The partitioning step results in a substantially exclusive transfer of the artemisinin into the acetonitrile layer with concomittant reduction in the amount of material, i.e., on the order of 32% to 36% of the original hexane extract. It will be appreciated that concentration of the sample to this extent materially decreases the workload of the silica columns used in the chromatography step of the inventive method. Prior to the evaporation step, for simplicity as well as for technical reasons, it is preferred to remove any water present in the acetonitrile phase. The water present may be removed by such commonly known means as azeotropic techniques using benzene and absolute alcohol or by using anhydrous sodium sulfate; however, it was discovered that water present can be efficiently and inexpensively removed by saturating the mixture with sodium chloride followed by removing the water as brine.

Subsequent evaporation of the non-aqueous acetonitrile phase yielded an oily, yellowish-brown, residue containing artemisinin of about three times richer than the hexane extract. For the reason that the acetonitrile phase is also rich in artemisinic (qinghao) acid, partial crystallization of the acid from this fraction is possible through the use of acetonitrile. In this manner, about 10% of the weight of the acetonitrile phase may be simply and practically removed prior to the chromatography step.

In the chromatography step of the invention, a ratio of 1:10 (solute to absorbent) was discovered to yield excellent results. In the known chromatographic techniques, a ratio of substantially 1:44 has been required. In the solvent system of the invention, a mixture of ethyl acetate in the range of about 10% to 20% in hexane was found to be quite effective. Using the solvent system and technique of the invention, the elution of the acid is reversed when compared with the mechanics of a solvent system consisting of 5% to 7.5% ethyl acetate in chloroform. In other words, using the method of the invention, the acid elutes first followed by the artemisinin. Accordingly, substantially all of the acid present will be removed prior to elution of artemisinin thus enhancing the purity of the artemisinin finally recovered in the process. By way of example of the chromatographic step of the process elution of the artemisinic acid and artemisinin from the column required the use of one column volume of each of the eluting solvent systems consisting of 10% ethyl acetate/hexane and 15% ethyl acetate/hexane, followed by 20% ethyl acetate/hexane (one and one half column volume) at a filtration flow rate. Artemisinic acid was present in the fraction eluted with 10% ethyl acetate/hexane (one column volume) and 15% ethyl acetate/hexane (two third column volume). Artemisinin was obtained from the oily greenish-yellow fraction eluted with 15% ethyl acetate/hexane (one third column volume) and 20% ethyl acetate/hexane (one and one half column volume). Purification of artemisinin was carried by crystallization from ether/hexane (1:4) with a further purification by recrystallization from methylene chloride/ hexane (1:4).

As mentioned hereinbefore, one of the major advantages, particularly economic, of the process of the invention is that the packing material in the columns may be used in at least two runs. After each use, a simple washing, for example, using one and one-half column volumes of ethyl acetate will recondition the column. The polarity of the solvent system should be decreased in a succeeding run to compensate for the partial deactivation of the silica gel.

In accordance with the description hereinabove, the solvent composition used in a second run would be about 8% ethyl acetate in hexane (one column volume) 13% ethyl acetate in hexane (one column volume) and 18% ethyl acetate in hexane (one and one half column volume), thus compensating for the slight deactivation of the silia gel from the first run. The silica gel used as a packing material in the examples herein was Machery Nagel silica gel 60, Brinkmann, mesh size 70–270. The recovered ethyl acetate/hexane solvent mixture may be used over and over again after drying, for example, over anhydrous sodium sulfate (250g/3L) and adjusting its composition to the desired percentage level.

The following examples illustrate specific embodiments of the method of the invention.

EXAMPLE I

Dried unground leaves of *Artemisia annua* (250g) was extracted by continuous hot percolation over a period of 48 hours using n-hexane as a solvent. The solvent free extract (19.5g, 7.8%) was partitioned with n-hexane and 20% aqueous acetonitrile, presaturated with each other, using 12ml hexane per gram extract and one third of this amount (4 ml/g) of the 20% aqueous acetonitrile phase. Partitioning of the hexane phase between 20% aqueous acetonitrile was repeated two additional times using the same solvent ratio. The combined 20% aqueous acetonitrile was back-washed using 10% of its volume with presaturated hexane (24ml). Sodium chloride (7g/100ml of 20% aqueous acetonitrile) was added to remove the water. Evaporation of the acetonitrile in vacuo provided 6.7g of an oily yellowish-brown residue. About 650 mg of artemisinic acid was crystallized from this acetonitrile phase and removed prior to chromatography. Column chromatography of the residue was conducted using Machery Nagel silica gel 60 (Brinkmann, mesh size 70–270) in the ratio of 1:10. The eluting system comprising 10% ethyl acetate/hexane (1:0 column volume), followed by 15% ethyl acetate/hexane (1.0. column volume) and 20% ethyl acetate/hexane (one and one-half column volume), at filtration flow rates, yielded artemisinin in the column fractions eluted with 15% ethyl acetate/hexane (last ⅓of the column volume-)and 20% ethylacetate/hexane (1.5 column volume). Evaporation of the solvent produced 2.5g of a greenish-yellow oil that crystallized readily from ether/hexane (1:4) to yield 270mg of pure artemisinin.

The above procedure was repeated three times on the same scale and consistently provided the same yields of artemisinin.

EXAMPLE II

Unground leaves of *Artemisia annua* (400kg) were proportionally extracted, partitioned and chromatographed in accordance with the procedure of Example I. The weight of the soluble hexane extract was 29.2kg (7.3%) and that of the acetonitrile phase, 10.765kg (36.8% that of the hexane extract). Partial crystallization of artemisinic acid from the acetonitrile phase (using 680ml acetonitrile/kg) yielded 1.18kg. The total amount of isolated artemisinin from this 400kg batch was 485g.

EXAMPLE III

The extraction and partitioning of the hexane extract was carried out as described in Example I. A portion of the acetonitrile residue (466g) obtained from Example II was column chromatographed on fresh silica gel 60 (4.5kg, 18×41cm) yielding an artemisinin rich fraction (wt 72.6g) from which 23.45g of pure artemisinin was obtained (0.135%).

EXAMPLE IV

The extraction, partitioning and chromatography was carried out as described under Example III except that the silica gel 60 was reused. 452g of the acetonitrile phase was applied on a reused silica gel 60 column (4.5kg, 18×41cm) to yield an artemisinin rich fraction having a weight of 70.22g from which 22.15g of artemisinin was obtained (0.132%).

EXAMPLE V

The dried hexane extract (12.5g) from 160g of the dried unground leaves of *Artemisia annua* was partitioned and chromatographed in accordance with the procedure of Example I. The acetonitrile phase, after evaporation to dryness, yielded a 6.3g residue. The residue, upon chromatography, provided an artemisinin containing fraction (2.24g) from which 170mg of pure artemisinin was obtained (0.106%).

EXAMPLE VI

The dried hexane extract (12.5g) from 160g of the dried unground leaves of *Artemisia annua* was partitioned using non-saturated phases of hexane and 20% aqueous acetonitrile, and then chromatographed as described in Example I. The acetonitrile phase, after evaporation to dryness, yielded a 4.05g residue. The residue upon being chromatographed, yielded an artemisinin containing fraction (0.75g) from which 137mg of pure artemisinin was obtained (0.085%).

EXAMPLE VII

The dried hexane extract (12.5g) from 160g of the dried unground leaves of *Artemisia annua* was partitioned using saturated phases of hexane and 20% aqueous acetonitrile. The 20% aqueous acetonitrile was evaporated directly without salting out the water with sodium chloride, then chromatographed in accordance with the procedure of Example I.

The acetonitrile phase, after evaporation, yielded a 4.5g residue. The residue, upon being chromatographed, yielded an artemisinin containing fraction (1.34g) from which 121mg of pure artemisinin was obtained (0.075%).

EXAMPLE VIII

Dried hexane extract (12.5g) from 160g of the unground dried leaves of *Artemisia annua* was partitioned using unsaturated phases of hexane and 20% aqueous acetonitrile. In this example, 20% aqueous acetonitrile was not back-washed with 10% of its volume with hexane and was directly evaporated without removing the water. This procedure yielded a 4.6g residue. The residue, upon being chromatographed in accordance with the procedure of Example I, yielded an artemisinin containing fraction (1.59g) from which 111mg of pure artemisinin was obtained (0.069%).

EXAMPLE IX

Dried hexane extract (obtained as under Example I), about 20g from 250g of Artemisia annua unground leaves, was partitioned between 240ml of hexane and 3×80ml of acetonitrile (both presaturated with each other). The combined acetonitrile fraction was backwashed with 24ml of hexane followed by evaporation in vacuo at 40° producing a 9.7g residue. Artemisinin remained exclusively in the acetonitrile phase. Chromatography, in accordance with the procedure of Example I, yielded 250 mg of artemisinin (0.1% isolated yield).

The dry hexane extract of the plant leaves obtained as in Example I was partitioned between 10% aqueous methanol and hexane, presaturated with each other. A thin layer chromatographic analysis of the methanolic and hexane phases on silica gel G revealed that artemisinin was distributed between the methanolic phase and the hexane phase, accordingly this procedure is not feasible. In another approach, dry hexane extract of the leaves was dissolved in methanol and an aqueous solution of lead subacetate added. A sticky residue deposited itself at the bottom of the decanter permitting easy decantation of the supernate. The residue was washed with methanol. The supernate and the methanol wash were combined, evaporated to dryness and the residue extracted with chloroform. Chromaography of the residue obtained from the chloroform fraction yielded artemisinin in such low yields as to represent no improvement over the art.

It will be appreciated from the examples that the method of the invention, as exemplified in Examples I through IX, provide pure artemisinin simply and practically in yields heretofore unobtainable in the methods known in the art and the other methods attempted by the inventors.

We claim:

1. The process of producing artemisinin from the plant *Artemisia annua* comprising the steps of extracting the plant with hexane, partitioning the hexane extract between hexane and acetonitrile - water mixture, evaporation of the solvents to dryness, chromatographing the evaporated mixture on silica gel adsorbent with a solvent comprising ethyl acetate in hexane, and evaporating the acetonitrile phase followed by crystallization to produce substantially pure artemisinin.

2. The process of claim 1 wherein the dried leaves only of the plant is used.

3. The process of claim 1 wherein said hexane extract of the leaves of *Artemisia annua* is partitioned between presaturated hexane and aqueous acetonitrile.

4. The process of claim 3 wherein the 20% aqueous acetonitrile is used.

5. The process of claim 3 comprising the step of removing water from the partitioned extract prior to evaporation of the solvents to dryness.

6. The process of claim 3 comprising the step of saturating the partitioned mixture with sodium chloride followed by removing water from the mixture as brine.

7. The process of claim 3 comprising the step of crystallizing artemisinic acid out of the partitioned mixture prior to chromatographic step.

8. The process of claim 1 wherein the chromatographic step is carried out in columns having a solute to adsorbent ratio of about 1:10.

9. The process of claim 1 wherein chromatographic solvent comprises a mixture of about 10% to 20% ethyl acetate in hexane.

10. The process of claim 1 wherein the chromatographic step utilized one column volume of each of 10% ethyl acetate in hexane and 15% ethyl acetate in hexane, followed by one and one half column volume of 20% ethyl acetate in hexane.

11. The process of producing artemisinin from the plant *Artemisia annua* comprising the steps of extracting the dried leaves of the plant with hexane, Partitioning the hexane extract with about 20% aqueous acetonitrile in presaturated hexane thereby transferring artemisinin present into the acetonitrile phase, saturating the mixture with sodium chloride followed by removing the water from the mixture as brine, evaporating the acetonitrile phase to produce an oily residue, crystallizing artemisinic acid out using acetonitrile, evaporating the acetonitrile, chromatographing the residue over silica columns using a ratio of about 1:10 solute to adsorbent and a solvent system comprising a mixture of about 10% to 20% ethyl acetate in hexane to obtain an oily material, crystallizing substantially pure artemisinin from said oily material.

12. The method of claim 10 wherein the oily material obtained from the chromatographic step is subjected to treatment with an ether/hexane mixture to obtain crystalline artemisinin followed by recrystallization of said crystalline artemisinin with a mixture of hexane and methylene chloride to produce pure artemisinin.

* * * * *